(12) United States Patent
Johannison et al.

(10) Patent No.: US 8,519,211 B2
(45) Date of Patent: Aug. 27, 2013

(54) WOUND PAD COMPRISING A BODY OF COMPRESSED OPEN-CELLED FOAM MATERIAL

(75) Inventors: Ulf Johannison, Landvetter (SE); Magnus Paledzki, Mölnlycke (SE); Eva-Karin Daun, Lerum (SE)

(73) Assignee: Mölnlycke Health Care AB, Göteborg (SE)

( * ) Notice: Subject to any disclaimer, the term of this patent is extended or adjusted under 35 U.S.C. 154(b) by 0 days.

(21) Appl. No.: 13/378,495

(22) PCT Filed: Jun. 3, 2010

(86) PCT No.: PCT/SE2010/050609
§ 371 (c)(1),
(2), (4) Date: Feb. 16, 2012

(87) PCT Pub. No.: WO2010/147535
PCT Pub. Date: Dec. 23, 2010

(65) Prior Publication Data
US 2012/0136328 A1    May 31, 2012

(30) Foreign Application Priority Data
Jun. 15, 2009    (SE) .................................... 0950461

(51) Int. Cl.
*A61B 19/00*    (2006.01)
(52) U.S. Cl.
USPC .................. 604/359; 604/358; 604/317
(58) Field of Classification Search
None
See application file for complete search history.

(56) References Cited

U.S. PATENT DOCUMENTS

| 3,665,918 | A | 5/1972 | Lindquist | 128/156 |
| 3,978,855 | A | 9/1976 | McRae | 128/156 |
| 4,788,972 | A | 12/1988 | DeBusk | 128/89 |
| 5,685,834 | A | 11/1997 | Barth | 602/75 |
| 6,495,229 | B1 | 12/2002 | Carte | 428/40.1 |
| 2001/0034499 | A1 | 10/2001 | Sessions | 602/46 |

(Continued)

FOREIGN PATENT DOCUMENTS

| EP | 0888137 | 5/2004 |
| GB | 1253845 | 11/1971 |

(Continued)

OTHER PUBLICATIONS

International Preliminary Report on Patentability issued Dec. 16, 2011 for International Patent Application No. PCT/SE2010/050609, which was filed Jun. 3, 2010 and which was published on Dec. 23, 2010 as WO 2010/147535 [Inventor—Johannison; Applicant—Molnlycke Health Care AB] [pp. 1-4].

(Continued)

*Primary Examiner* — Leslie Deak
*Assistant Examiner* — Sara Sass
(74) *Attorney, Agent, or Firm* — Ballard Spahr LLP

(57) ABSTRACT

An absorbent article, such as a wound pad, comprising a body of compressed thermoplastic or thermo-set open-celled foam is described, wherein the body has a pattern of ultrasonically made depressions in two opposite sides thereof, the depressions in the opposite sides being coaxial to each other and separated from each other by a common bottom portion which is compressed to a higher extent than the remaining parts of said body. A method for manufacturing such a body is also described.

11 Claims, 2 Drawing Sheets

(56) References Cited

U.S. PATENT DOCUMENTS

| | | |
|---|---|---|
| 2002/0002209 A1 | 1/2002 | Mork .......................... 521/61 |
| 2004/0127837 A1 | 7/2004 | Sigurjonsson ............. 602/43 |
| 2005/0124709 A1* | 6/2005 | Krueger et al. ............ 521/50 |
| 2005/0142334 A1 | 6/2005 | Mikata et al. ............. 428/190 |
| 2007/0148433 A1* | 6/2007 | Mallory et al. ........... 428/304.4 |
| 2007/0161936 A1 | 7/2007 | Svetlik ....................... 602/46 |

FOREIGN PATENT DOCUMENTS

| | | |
|---|---|---|
| GB | 1417962 | 12/1975 |
| GB | 2276087 | 9/1994 |
| GB | 2428581 | 2/2007 |
| WO | WO 03/045296 | 6/2003 |
| WO | WO 2005/021622 | 3/2005 |

OTHER PUBLICATIONS

International Search Report issued Sep. 17, 2010 for International Patent Application No. PCT/SE2010/050609, which was filed Jun. 3, 2010 and which was published on Dec. 23, 2010 as WO 2010/147535 [Inventor—Johannison; Applicant—Molnlycke Health Care AB] [pp. 1-4].

Written Opinion issued Sep. 17, 2010 for International Patent Application No. PCT/SE2010/050609, which was filed Jun. 3, 2010 and which was published on Dec. 23, 2010 as WO 2010/147535 [Inventor—Johannison; Applicant—Molnlycke Health Care AB] [pp. 1-3].

Extended European Search Report issued May 22, 2013 by the European Searching Authority for Application EP 10789813.

\* cited by examiner

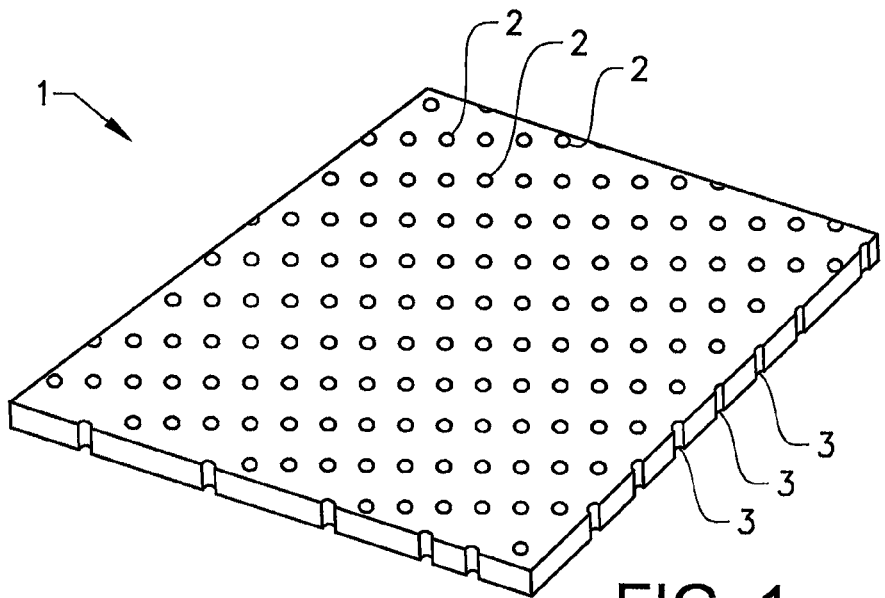
FIG. 1
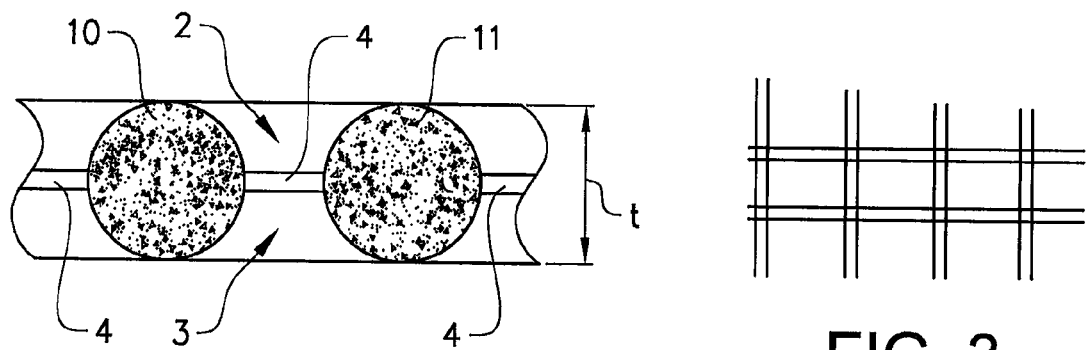
FIG. 2
FIG. 3
FIG. 4
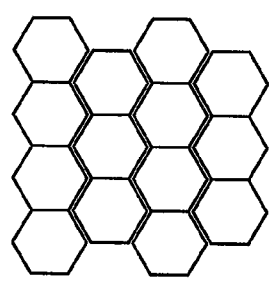
FIG. 5

WOUND PAD COMPRISING A BODY OF COMPRESSED OPEN-CELLED FOAM MATERIAL

CROSS REFERENCE TO RELATED APPLICATIONS

The present application is a National Phase Application of International Application No. PCT/SE2010/050609, filed Jun. 3, 2010, which claims priority to Swedish Patent Application No. 0950461-4, filed Jun. 15, 2009, which applications are incorporated herein fully by this reference.

TECHNICAL FIELD

The present invention relates to a wound pad comprising a body of compressed open-celled foam of thermoplastic or thermo set material and a method for manufacturing such a wound pad.

BACKGROUND OF THE INVENTION

The main function of a wound pad is to remove excessive exudate from a wound bed and prevent the removed exudate from returning to the wound bed if the wound pad is subjected to gravity forces or other external forces. A wound pad shall thus have good liquid acquisition properties (i.e. it should be easy for exudate to enter the wound pad), good liquid retention or holding properties (i.e. ability to prevent the exudate sucked up by wound pad to be pressed back to the wound bed by gravitational or other external forces). Furthermore, the absorption capacity, i.e. the amount of exudate that can be stored in the pad in a relaxed state thereof, is important as well as spreading or distribution property, i.e. the ability of the pad to transport exudate in directions parallel to the plane of the upper surface of the wound bed. Finally, the wound pad shall also provide a moist environment above the wound bed for promoting wound healing.

Thermoplastic and thermo-set open-celled foams as well as cellulose-based materials are often used as absorbent articles, such as wound pads or parts thereof. Foams typically have very good liquid wicking properties, i.e. ability to transport exudate away from the wound bed in directions perpendicular to the plane thereof, but relatively poor spreading properties. These poor spreading properties are associated with the risk that such a foam, when used as a wound pad, will be locally saturated and leak long before the theoretical absorption capacity of the foam is reached, which results in exudate getting back down to the wound bed and causing damage to the surrounding skin, a phenomenon often referred to as maceration. It is known, see for example WO 2005/021622, to improve the spreading properties of foams by partly or wholly compress foams using heat and pressure to re-orientate a majority of the cells to ellipsoidal cell shape. Such a compression will lead to improved retention properties but impaired absorption capacity as well as liquid acquisition properties due to the decrease in cell sizes.

Compression also leads to a stiffening of the foam so that a too high degree of compression will negatively influence the conformability of a wound pad, i.e. the ability of the wound pad to conform to the contour of the part of the body of a patient to which a wound dressing containing such a wound pad is applied.

It is for both practical and aesthetic reasons desirable that wound pads are thin. However, a thin body of uncompressed foam material tends to have too poor absorption and retention properties to be used as a wound pad or as a layer in a wound pad.

It is an objective of the present invention to provide a wound pad comprising a body of compressed open-celled foam of thermoplastic or thermo-set material, which has good conformability, spreading, retention and liquid acquisition properties and adequate absorption capacity as well as a method for manufacturing such a wound pad enabling a variation of the combined spreading, retention and liquid acquisition properties of the body without sacrifice of conformability.

SUMMARY OF THE INVENTION

These objectives are obtained by an absorbent article, such as a wound pad, comprising a body of compressed thermoplastic or thermo-set open-celled foam, characterised in that said body has a pattern of ultrasonically made depressions in two opposite sides thereof, the depressions in the opposite sides being coaxial to each other and separated from each other by a common bottom portion which is compressed to a higher extent than the remaining parts of said body. In such a body, the compression of the foam will be larger in regions surrounding the depressions than in other regions of the body which means that the spreading and retention of such a body to a great extent can be varied by varying the pattern of depressions. Furthermore, the presence of regions between the depressions having a lower compression makes the body very conformable in spite of the high compression in the areas close to the bottom portions.

In a preferred embodiment, in a region around each depression, the size of the cells increase in a direction from said common bottom portion to the respective opening of the depression, as well as in an outward direction from said common bottom portion parallel to the surfaces of said body containing said depressions.

In order to provide a desired conformability of such a body, the common bottom portions of the depressions in the patterns of depression are unconnected to each other and distanced at least 10% of the thickness of said body.

The patterns of depressions can be regular but irregular patterns or different depths of the depressions can also be used.

The material in the bottom portions of the depression can preferably be fused together so that only a small amount of very small cells are present in the common bottom portions.

In the preferred embodiment, said body is made of polyurethane foam but other foams of thermo-set or thermoplastic material can alternatively be used.

One or more layers of absorbent material can be used in combination with the foam body.

The invention also relates to a method of manufacturing an absorbent article, such as a wound pad, comprising a body of open-celled foam of thermoplastic or thermo-set material, characterised by forming a pattern of depressions in two opposite sides of a web of foam of thermoplastic or thermo-set material, the depressions in the opposite sides being coaxial to each other and separated from each other by a bottom portion, by feeding said web between a counter roller having a pattern of protrusions projecting from its outer surface and a horn of an ultrasound welding device, optionally applying one or more layers of absorbent material on at least one side of said web and attaching said layers to said web, and cutting individual wound pads from the web of compressed thermoplastic or thermo-set material and optionally superposed layers of absorbent material.

The invention further relates to a wound dressing comprising an absorbent article as described above.

BRIEF DESCRIPTION OF THE DRAWINGS

The invention will now be described with reference to the enclosed figures, of which;

FIG. 1 schematically discloses a foam body useful as a wound pad or as a component of a wound pad according to a preferred embodiment of the invention, FIG. 2 schematically discloses a sectional view of a part of the body according to FIG. 1, FIGS. 3-5 schematically disclose different patterns of depressions that can be used in further embodiments of the invention, FIG. 6 schematically discloses an ultrasonic welding device for manufacturing a compressed body of open-celled thermoplastic or thermo-set material according to an embodiment of the invention, and FIG. 7 schematically discloses parts of a counter roller and a horn of the ultrasonic welding device in FIG. 6.

DESCRIPTION OF EMBODIMENTS

Figure 6:
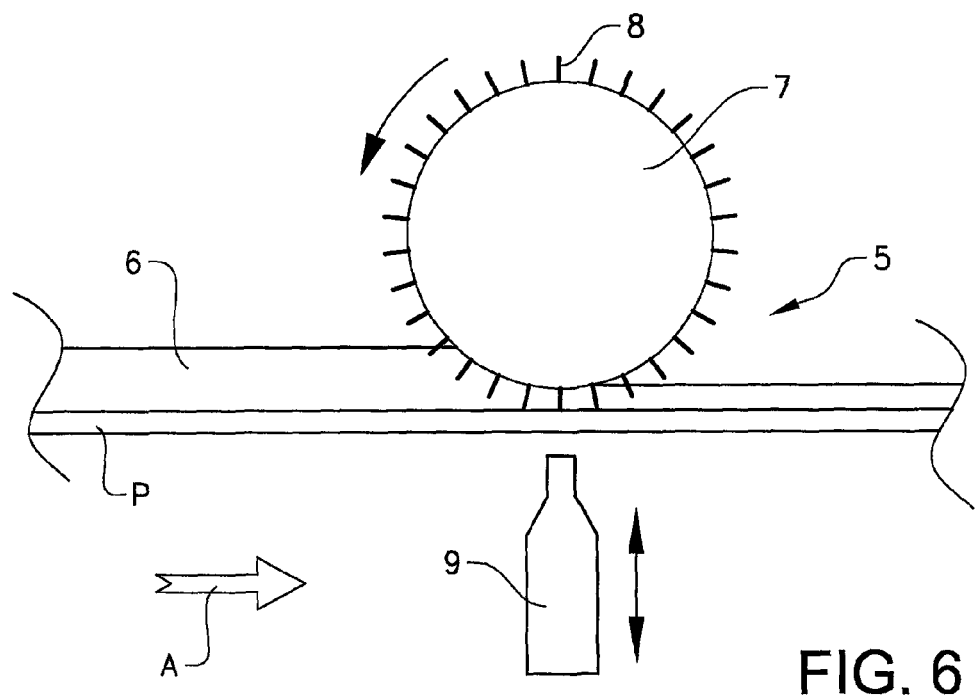

In FIG. 1 is schematically shown a body 1 of compressed open-celled polyurethane foam. Body 1 has a pattern of depressions in opposing upper and lower sides. The terms "upper" and "lower" refers to the body as shown in the figure and is independent of how a wound dressing comprising such a body is located on a body of a patient. The depressions in the upper side of body 1 are given the reference sign 2 and the depressions on the lower side are given the reference sign 3.

The depressions 2 in the upper side of the body are coaxial to the depressions 3 in the lower side of body 1, which means that the patterns on the upper and lower sides are similar to each other. In the shown embodiment also the sizes of the depressions 2, 3 in both the patterns are identical but as will be explained later the depth of opposite depressions can slightly vary. The opposite depressions 2, 3 in the upper and lower side, respectively, are separated from each other by a common bottom portion 4 (as shown in FIG. 2).

An ultrasonic welding device 5 for manufacturing the body 1 shown in FIGS. 1 and 2 is schematically shown in FIG. 6. The body 1 is manufactured by feeding a web 6 of uncompressed open-celled polyurethane foam between a counter roller 7 having a pattern of protrusions 8 projecting from its outer surface and a horn 9 of the ultrasound welding device 5 and thereafter cutting the web into discrete bodies 1. A process paper P is preferably used to decrease friction between the ultra-sonic welding device and the web of foam. Optionally one or more layers of absorbent material can be applied on one side of or both sides of said web and be attached thereto before the cutting step in order to manufacture composite wound pads comprising two or more layers. The ultrasonic welding device 5 can be of a commercially available type, such as 2000X (20 kHz) from Branson, DPC (20 kHz) from Dukane, or 2000 cs (20 kHz) from Herrmann.

Equipment for feeding the web 6 in the direction of arrow A and for superposing optional layers in order to form a composite wound pad, as well as cutters, are well known to the skilled man. The described equipment for manufacturing of wound pads can be a separate process line or placed in a continuous process line for the manufacturing of wound dressings comprising such pad.

Figure 7:
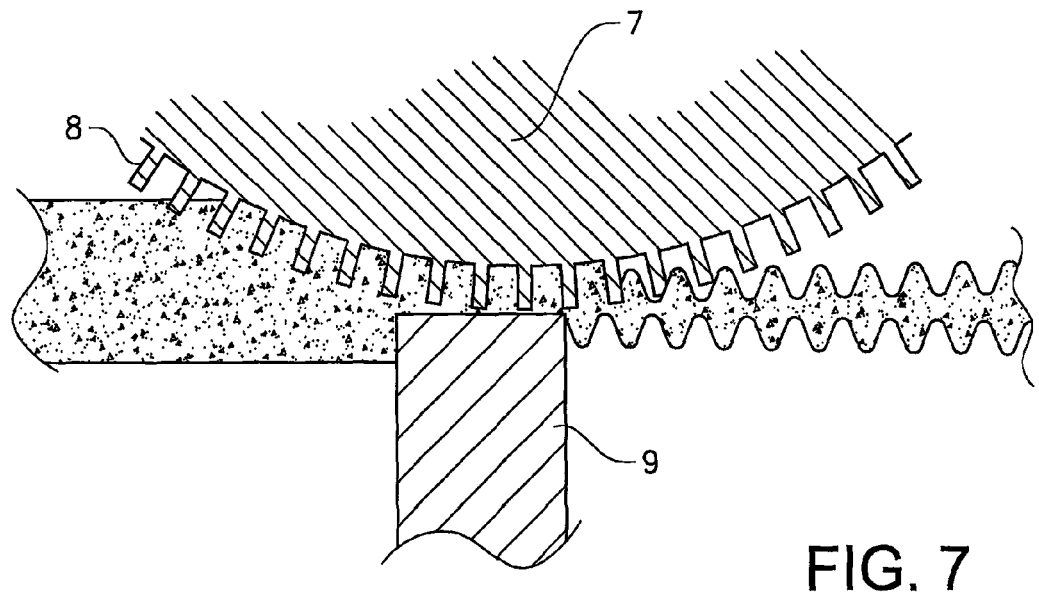

In FIG. 7 a part of the counter roller 7 and the horn 9 of the ultrasonic welding device 5 is schematically shown in a larger scale when the horn is in closest position to the projections on the counter roller 7. The horn 9 moves towards and away from the counter roller at an ultrasonic frequency. This hammering on the web will cause heat to be developed in the material due to internal friction. The heat created will be concentrated to the foam disposed between the tips of the protrusions 8 and the horn 9. Spreading of heat from this area will be very limited. The energy delivered by the ultrasonic welding device 5 is so high that the material between the tips of the protrusions 8 and the horn 9 is fused together so that no cells or very small cells are left in these portions of the web after the compression step with the ultrasonic welding device. The preferably used process paper P is not shown in FIG. 7.

It has been shown that a body 1 manufactured as above and having the material in the common bottom portions 4 fused together attained the configuration schematically shown in the sectional view of FIG. 2. In the regions 10, 11 outside of the depressions 2, 3, the cell sizes are smallest in the portions being closest to the bottom portions 4 and increase gradually in an upward and downward direction as well as a lateral direction there from. As is evident from FIG. 2, the lower part and upper part of regions 10 and 11 have the same configuration in spite of the lower parts being differently compressed during the passage of the foam web 6 through the ultrasonic welding device 5.

This suggests that the compression in the foam obtained by the described manufacturing method is not an effect of permanent deformation of cells in the foam due to application of heat and pressure but instead an effect of that in the vicinity of the bottom portions 4 the foam is prevented from resiliently recover its initial thickness by the fusing together of the foam in the common bottom portions. This effect is considered to be similar to the effect of depressing a finger in a foam mattress or the like and which is, for example, used in cushions having patterns of depressions in which the expansion of the bottom portions in such depressions are prevented by buttons sewed thereto. It has also been found that if the common bottom portion is removed, the foam material around the hole created by the removal of the bottom portion will resiliently recover to its initial thickness or to a thickness near its initial thickness so that said hole will have a cylindrical wall.

Thus, the uppermost and lowermost parts of the regions outside the bottom portions 4 will have the largest cell sizes and these parts have the best liquid acquisition properties. Since the cell sizes decrease in all directions from these parts, exudate entering these parts will be drawn into the central parts of the body 1 by capillary forces. The body 1 has liquid acquisition properties equal to the liquid acquisition properties of an uncompressed foam body of the same material. Due to the smaller cell sizes in central region of the body parallel to the upper and lower surfaces thereof, the retention property of body 1 is also good. Furthermore, the cell size gradient in such a central region also ensures a good spreading of the exudates drawn into the body 1.

Due to the relatively low compression of the material in parts furthest from the bottom portions 4, the conformability of the foam material can be maintained in spite of the high compression in the bottom portions and in parts in the vicinity thereof.

The body schematically disclosed in FIGS. 1 and 2 has been manufactured by feeding a web of uncompressed open-celled polyurethane foam MCF 03 from Corpura BV, Etten-Leur, NL having a thickness of 5 mm through the gap between the horn of the ultrasonic welding device DPC (20 kHz) from Dukane and a counter roller having rows of cylindrical protrusions extending around the peripheral surface thereof in a regular pattern. The height of each protrusion was 1 mm and the diameter was 1.26 mm. The distance between adjacent protrusions was 3 mm and between the rows was 2.6 mm. After passage of the ultrasonic welding device 5, the thickness t of the web was 2.5 mm.

An example of a suitable process paper used is polyethylene coated paper (120 g/m$^2$) from Mondi Silicart.

After passage of the welding device 5, the web was cut into individual bodies 1. Each body 1 had a pattern of depressions as shown in FIG. 1 in which the bottom portions were circular and had the same diameter as the tips of the protrusions projecting out from the counter roller 7. The bottom portions in each row were distanced 3 mm from each other and the distance between adjacent rows in the pattern was 2.6 mm.

Such bodies 1 were compared with bodies of the same foam material that was uncompressed and had the same thickness as the web 6 before entering the ultrasonic welding device 5 and with bodies evenly compressed by heat and pressure to the same thickness t as the bodies 1. It was surprisingly found that bodies 1 had as good liquid acquisition properties as bodies of uncompressed foam and far better liquid acquisition properties than the evenly compressed foam bodies. Furthermore, the bodies 1 had as good retention properties as the evenly compressed foam bodies. Also the spreading of absorbed liquid was of the same magnitude as for the evenly compressed foams while it was better than for the uncompressed foam.

For determining the conformability of bodies 1, extensibility (i.e. the force needed to extend the test piece a certain distance) and the bending length was measured for uncompressed bodies, evenly compressed bodies and bodies 1 according to the described embodiment. The bending length is a test for deciding drapability of a material and measures the length needed for a free end of a material to bend from its own weight a certain angle. These tests showed that the extensibility as well as the bending length was better for bodies 1 than for the uncompressed bodies and evenly compressed bodies.

The absorption capacity of bodies 1 was of course less than the absorption capacity of the uncompressed bodies but of the same magnitude as the evenly compressed bodies. However, since the uncompressed foam bodies have poor spreading properties, wound dressings having wound pads of uncompressed foam tend to leak locally long before absorbing an amount of liquid corresponding to their absorption capacity whereas compressed foam bodies do not leak until they have absorbed an amount of liquid in the vicinity of their absorption capacity.

The liquid handling properties and the conformability of the bodies manufactured according to the present invention are for a given thickness of the uncompressed foam material to a high degree dependent on the distance between the bottom portions in each row of depressions and the distance between adjacent rows of depressions, i.e. of how dense the patterns of depressions are. If a denser pattern is used so that said distances are less than 0.5 mm for a foam having an uncompressed thickness of 5 mm, the thickness t of the bodies will decrease and the stiffness will increase resulting in bodies having too low conformability to be used in wound dressings. Furthermore, the liquid acquisition properties will also be relatively poor. If a sparser pattern is used, the thickness t of the bodies will increase and the retention and spreading properties of the bodies will be somewhat impaired. It is therefore preferred that these distances be less than 7 mm, and preferably less than 6 mm when such bodies are to be used in a wound dressing as a layer closest to the wound bed. The distances between adjacent bottom portions in the pattern of depressions should therefore preferably be 30-100%, such as 40-80% and most preferably, 50-70% of the uncompressed thickness of the foam.

The properties of a body manufactured according to the present invention are to some extent influenced by the length of the protrusions projecting from the counter roller 7 of the ultrasonic welding device. If higher protrusions are used the thickness of the compressed foam will be somewhat larger, leading to overall somewhat larger cell sizes and consequently somewhat impaired spreading properties. The height of the protrusions shall therefore not be more than 80% of the uncompressed thickness of the foam. The height of the protrusions has, however, not been seen to influence the overall appearance of the material, the bottom portions being located approximately in middle of the manufactured compressed foam independently of the different lengths of protrusions used.

The protrusions 8 have in the described preferred embodiment circular cross sections. It is of course possible to use protrusions having cross sections of other shapes, such oval, rectangular, square, triangular, etc.

It is also possible to use patterns in which the bottom portions have other shapes than spots. In FIGS. 3-5 examples of possible patterns are schematically shown in which the bottom portions is composed of different lines instead of having spot shape. In FIG. 3 is shown a pattern in the form of a grid pattern, in FIG. 4 is shown a pattern in which the pattern consists of rows of bottom portions having the shape of a v, and in FIG. 5 a pattern is shown in which the bottom portions are lines form a honeycomb pattern. The present invention is not limited to the shown patterns which only are given as not limiting examples, other patterns and bottom portions shapes being easily available for the skilled man.

The patterns shown and described above are regular but it is possible to form irregular patterns in which the distances between adjacent protrusions and/or rows of protrusions are varying in order to obtain different characteristics in different parts of the body or by having different shapes or lengths of the protrusions projecting from the counter roller. It is of course also possible to use a pattern being combinations of spot-shaped and line-shaped patterns.

As is known in the art, so called superabsorbent particles or fibres can be incorporated into the foam in order to enhance the storing and retention properties thereof Other examples of substances that could be added to the foam before or after compression or even during the manufacturing of the uncompressed foam to e.g. promote wound healing are:

a) an antimicrobial chosen from a group of Silver, Silver salts, Zink, Zink salts, Iodine, Iodine complexes, poly hexamethyl biguanide, chlorhexidine and/or any mixtures or combinations thereof; and/or b) any of the following: vitamins, peptides, growth factors, nucleic acids and/or mixtures or combinations thereof.

In the described preferred embodiments, the bottom portions are compressed to such extent that only very small cells remain therein, which is preferred when the compressed body shall be used as a wound pad. It is, however, possible to run the ultrasonic welding device so that the bottom portions are fused together to a lesser extent, thereby obtaining larger remaining cells in the bottom portions and possibly also a thicker foam. It has been shown that the thickness of the foam can be increased if the transport rate of the web of foam through the ultrasonic device is increased In the described embodiment the web 6 consisted of a web of uncompressed foam. It is of course possible to instead use a web of pre-compressed foam. Furthermore, a foam body with varying cell sizes, for example a foam with gradient in cell sizes, can be used.

Bodies 1 as described above can be used as wound pads alone or in combination with other absorbent layers.

A wound dressing comprising a foam body according to any of the examples described with reference to FIGS. 1-7 can have a spreading layer, for example a thin layer of tissue or nonwoven, on top of the foam body, the foam body and the spreading layer being enclosed by a top layer extending laterally beyond the wound pad consisting of a vapour-permeable and liquid-impermeable film of a suitable polymer preferably having a WVTR (Water Vapor Transmission Rate) of at least 2000 g/m$^2$ per 24 hours as measured by ASTM D 6701. A liquid permeable layer with low tendency to stick to a wound bed, such as net of polymer or a discontinuous layer of silicone adhesive, can preferably be disposed closest to the wound bed, and the peripheral part of the top layer is coated with a layer of adhesive, which preferably can be the same adhesive extending under the wound pad.

Alternatively, a layer of absorbent material being a mixture of absorbent fibres and superabsorbent particles or fibres can be disposed between the foam body and the spreading layer in such a wound dressing.

The described embodiments can of course be modified without leaving the scope of the present invention. The patterns of bottom portions can have other shapes than shown and the different regular patterns can be combined to irregular patterns. The uncompressed foam can be of a type having a gradient cell size, i.e. the sizes of the cells decrease in the thickness direction of the foam, whereby a foam compressed in accordance with the present invention will maintain a gradient structure so that it would have different properties in thickness regions on both sides of a plane through the bottom portions. The shape of the wound pad need not be square or rectangular but can have any shape, such as oval or circular, etc. The invention shall therefore only be limited by the content of the enclosed patent claims.

The invention claimed is:

1. An absorbent article comprising a body of compressed, thermoplastic or thermo-set open-celled foam comprising cells, wherein the body has a pattern of ultrasonically made depressions in two opposite sides thereof, the depressions in the opposite sides being coaxial to each other and separated from each other by a common bottom portion of the body which is compressed to a higher extent than the remaining parts of the body.

2. The absorbent article of claim 1, wherein, in a region around each depression, the size of the cells increase in a direction from the bottom portion to the respective opening of the depression.

3. The absorbent article of claim 2, wherein, in a region around each depression, the size of the cells increase in an outward direction from the bottom portion parallel to the surfaces of the body containing the depressions.

4. The absorbent article of claim 3, wherein the bottom portions of the depressions in the patterns of depression are unconnected to each other and a distance between adjacent bottom portions in the patterns of depressions are at least 10% of the thickness of the body.

5. The absorbent article of claim 1, wherein the patterns of depressions are regular.

6. The absorbent article of claim 1, wherein a material in the bottom portions of the depressions is fused together.

7. The absorbent article of claim 1, wherein said body comprises polyurethane foam.

8. The absorbent article of claim 1, further comprising one or more layers of absorbent material.

9. A method of manufacturing an absorbent article, the method comprising the steps of:
   a. feeding a web of thermoplastic or thermo-set open-celled foam material comprising cells between a counter roller having a pattern of protrusions projecting from its outer surface and a horn of an ultrasound welding device, thereby forming a pattern of depressions in two opposite sides of the web of thermoplastic or thermo-set open-celled foam material comprising cells, the depressions in the opposite sides being coaxial to each other and separated from each other by a common bottom portion of the web of thermoplastic or thermo-set open-celled foam material; and
   b. cutting individual wound pads from the web of compressed thermoplastic or thermo set material.

10. A wound dressing comprising the absorbent article of claim 1.

11. The method of claim 9, further comprising applying one or more layers of absorbent material on at least one side of the web and attaching the layers to the web.

* * * * *